United States Patent
Matsuo et al.

(10) Patent No.: US 10,046,104 B2
(45) Date of Patent: Aug. 14, 2018

(54) PERISTALTIC PUMP

(71) Applicant: Nikkiso Company Limited, Tokyo (JP)

(72) Inventors: Sumiaki Matsuo, Shizuoka (JP); Kunihiko Akita, Shizuoka (JP)

(73) Assignee: NIKKISO COMPANY LIMITED, Tokyo (JP)

( * ) Notice: Subject to any disclaimer, the term of this patent is extended or adjusted under 35 U.S.C. 154(b) by 554 days.

(21) Appl. No.: 14/688,064

(22) Filed: Apr. 16, 2015

(65) Prior Publication Data
US 2015/0217040 A1 Aug. 6, 2015

Related U.S. Application Data

(63) Continuation of application No. PCT/JP2013/078272, filed on Oct. 18, 2013.

(30) Foreign Application Priority Data

Oct. 19, 2012 (JP) .................. 2012-231968

(51) Int. Cl.
*F04B 43/08* (2006.01)
*A61M 1/36* (2006.01)
(Continued)

(52) U.S. Cl.
CPC .......... *A61M 1/3656* (2014.02); *A61B 5/6866* (2013.01); *F04B 43/0081* (2013.01);
(Continued)

(58) Field of Classification Search
CPC ............ F04B 43/1253; F04B 43/0081; A61M 1/3656; A61M 1/1086; A61M 1/1006;
(Continued)

(56) References Cited

U.S. PATENT DOCUMENTS 3,046,788 A 7/1962 Laimin
4,090,404 A 5/1978 Dupont
(Continued)

FOREIGN PATENT DOCUMENTS

EP 1666078 6/2006
EP 2749858 7/2014
(Continued)

OTHER PUBLICATIONS

Machine Translation of JPH0415938 (Feb. 10, 2010).*
(Continued)

*Primary Examiner* — Charles Freay
(74) *Attorney, Agent, or Firm* — The Dobrusin Law Firm, P.C.

(57) ABSTRACT

A peristaltic pump includes a mounting concave section 8a on which a peristaltically-actuated tube connected to an arterial blood circuit is mountable; a roller which compresses the peristaltically-actuated tube mounted on the mounting concave section in a radial direction and causes the peristaltically-actuated tube to be peristaltically actuated in a longitudinal direction such that a liquid therein is flowable in the arterial blood circuit; a load sensor that is able to detect displacement of the peristaltically-actuated tube 1a mounted on the mounting concave section in the radial direction; and blockage detecting means that is able to detect a blockage of the arterial blood circuit based on the displacement detected by the load sensor.

18 Claims, 9 Drawing Sheets

(51) Int. Cl.
*A61B 5/00* (2006.01)
*F04B 43/00* (2006.01)
*F04B 43/12* (2006.01)
*A61M 1/10* (2006.01)

(52) U.S. Cl.
CPC .. *F04B 43/1253* (2013.01); *A61B 2562/0247* (2013.01); *A61M 1/1006* (2014.02); *A61M 1/1039* (2014.02); *A61M 1/1086* (2013.01); *A61M 2205/332* (2013.01); *A61M 2205/3355* (2013.01); *A61M 2205/70* (2013.01)

(58) Field of Classification Search
CPC ............ A61M 1/1039; A61M 2205/70; A61M 2205/3355; A61M 2205/332; A61B 5/6866; A61B 2562/0247
See application file for complete search history.

(56) References Cited

U.S. PATENT DOCUMENTS

| | | | |
|---|---|---|---|
| 4,460,355 A | | 7/1984 | Layman |
| 4,498,843 A | * | 2/1985 | Schneider ......... A61M 5/14232 222/14 |
| 4,534,756 A | | 8/1985 | Nelson |
| 4,743,228 A | | 5/1988 | Butterfield |
| 4,762,518 A | | 8/1988 | Kreinick |
| 4,784,576 A | | 11/1988 | Bloom |
| 4,969,808 A | * | 11/1990 | Tsukada ............... F04B 43/1253 417/477.1 |
| 5,024,099 A | | 6/1991 | Lee |
| 5,215,450 A | | 6/1993 | Tamari |
| 5,336,051 A | | 8/1994 | Tamari |
| 5,356,378 A | | 10/1994 | Doan |
| 5,380,172 A | | 1/1995 | Ulbing |
| 5,429,483 A | | 7/1995 | Tamari |
| 5,501,665 A | * | 3/1996 | Jhuboo ............. A61M 5/16854 604/65 |
| 5,720,721 A | | 2/1998 | Dumas et al. |
| 5,813,842 A | | 9/1998 | Tamari |
| 5,814,004 A | | 9/1998 | Tamari |
| 5,827,223 A | * | 10/1998 | Butterfield ........ A61M 5/16859 604/65 |
| 5,920,054 A | | 7/1999 | Uber |
| 5,927,951 A | | 7/1999 | Tamari |
| 6,039,078 A | | 3/2000 | Tamari |
| 6,374,084 B1 | | 4/2002 | Fok |
| 6,423,029 B1 | * | 7/2002 | Elsberry ........... A61M 5/14276 604/65 |
| 6,497,680 B1 | | 12/2002 | Holst |
| 6,868,720 B2 | | 3/2005 | Lobdell |
| 7,004,924 B1 | * | 2/2006 | Brugger ............. A61M 1/3626 600/16 |
| 7,037,092 B2 | * | 5/2006 | Kagawa .................... F04B 9/02 417/476 |
| 7,462,163 B2 | * | 12/2008 | Yap ..................... A61M 1/0023 604/131 |
| 7,935,912 B2 | | 5/2011 | Arima |
| 8,011,905 B2 | | 9/2011 | Artsyukhovich |
| 9,004,886 B2 | | 4/2015 | Beck |
| 9,662,433 B2 | | 5/2017 | Matsu |
| 2002/0151838 A1 | | 10/2002 | Beck et al. |
| 2003/0214412 A1 | | 11/2003 | Ho |
| 2008/0154095 A1 | | 6/2008 | Stubkjaer |
| 2010/0049134 A1 | | 2/2010 | Schuman, Jr. |
| 2010/0106466 A1 | | 4/2010 | Frohlich |
| 2010/0203179 A1 | | 8/2010 | Kaushik |
| 2011/0130741 A1 | | 6/2011 | Miles |
| 2011/0230814 A1 | | 9/2011 | Kopperschmidt et al. |
| 2012/0082576 A1 | | 4/2012 | Beck |
| 2014/0219829 A1 | | 8/2014 | Matsuo et al. |
| 2015/0238677 A1 | | 8/2015 | Akita et al. |

FOREIGN PATENT DOCUMENTS

| | | |
|---|---|---|
| JP | S56-113083 A | 9/1981 |
| JP | S64-022357 | 2/1989 |
| JP | H03-001290 | 1/1991 |
| JP | H04-015938 | 2/1992 |
| JP | 2003-265601 A | 9/2003 |
| JP | 2004/049494 | 2/2004 |
| JP | 2004-187990 | 7/2004 |
| JP | 2008-000425 A | 1/2008 |
| JP | 2008-002388 A | 1/2008 |
| JP | 2008-208808 | 9/2008 |
| JP | 2008-289635 A | 12/2008 |
| JP | 2010-188170 A | 9/2010 |
| JP | 2011-030880 A | 2/2011 |
| JP | 2012-192100 A | 10/2012 |
| WO | WO1994/028309 | 12/1994 |
| WO | 9710013 | 3/1997 |
| WO | 2007/093064 A1 | 8/2007 |

OTHER PUBLICATIONS

International Search Report, Application No. PCT/JP2013/078272, dated Jan. 21, 2014.
International Search Report, Application No. PCT/JP2013/078271, dated Jan. 21, 2014.
Potentially Related U.S. Appl. No. 14/186,193, published as 2014/0219829, published on Aug. 7, 2014.
Translation of International Search Report, Application No. PCT/JP2012/070614, dated Sep. 11, 2012.
Extended European Search Report dated Apr. 8, 2015 for Application No. 12826289.
Supplementary European Search Report dated May 27, 2016 for Application No. PCT/JP2013078272.

* cited by examiner

[Fig 1]
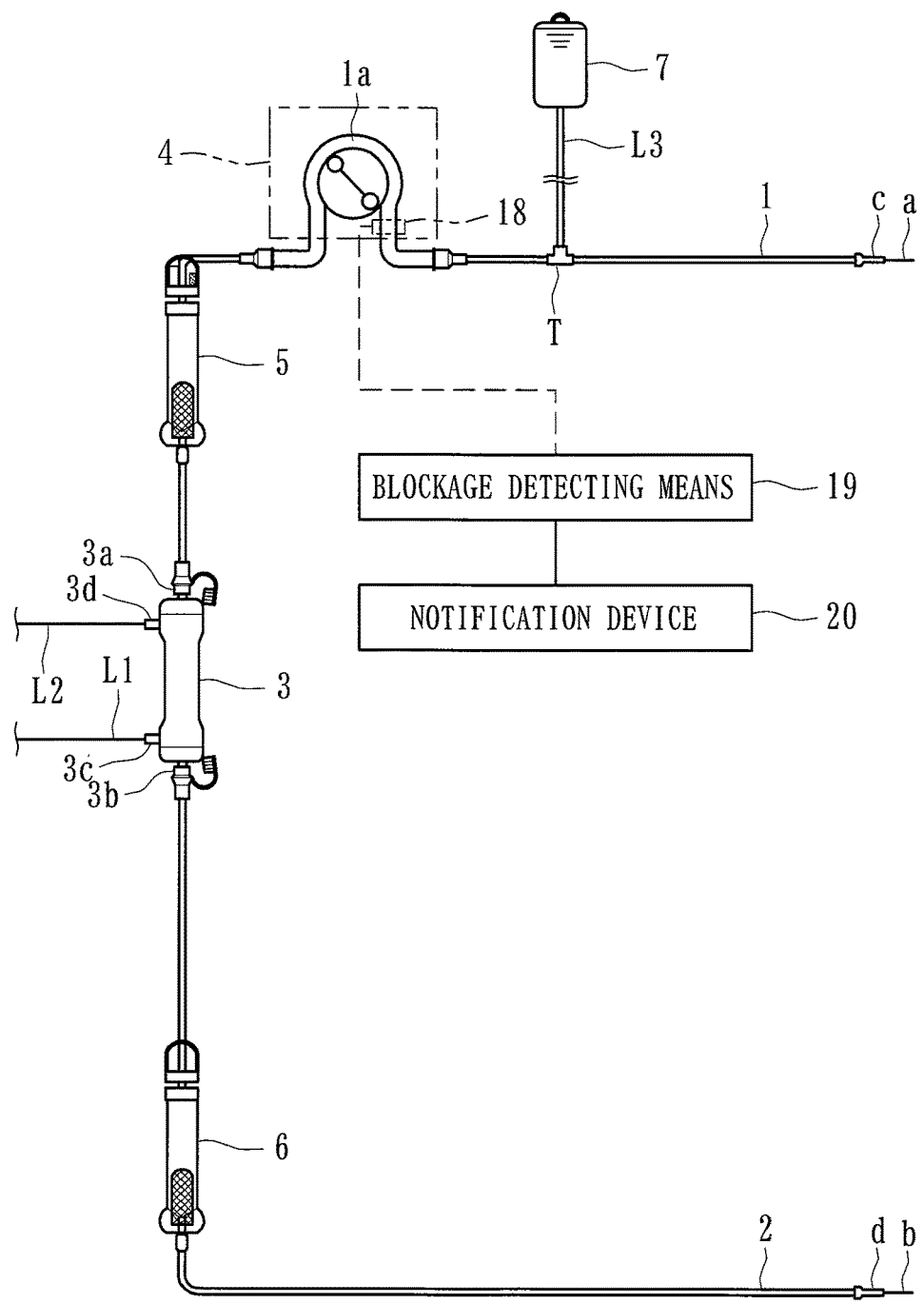

[Fig 2]
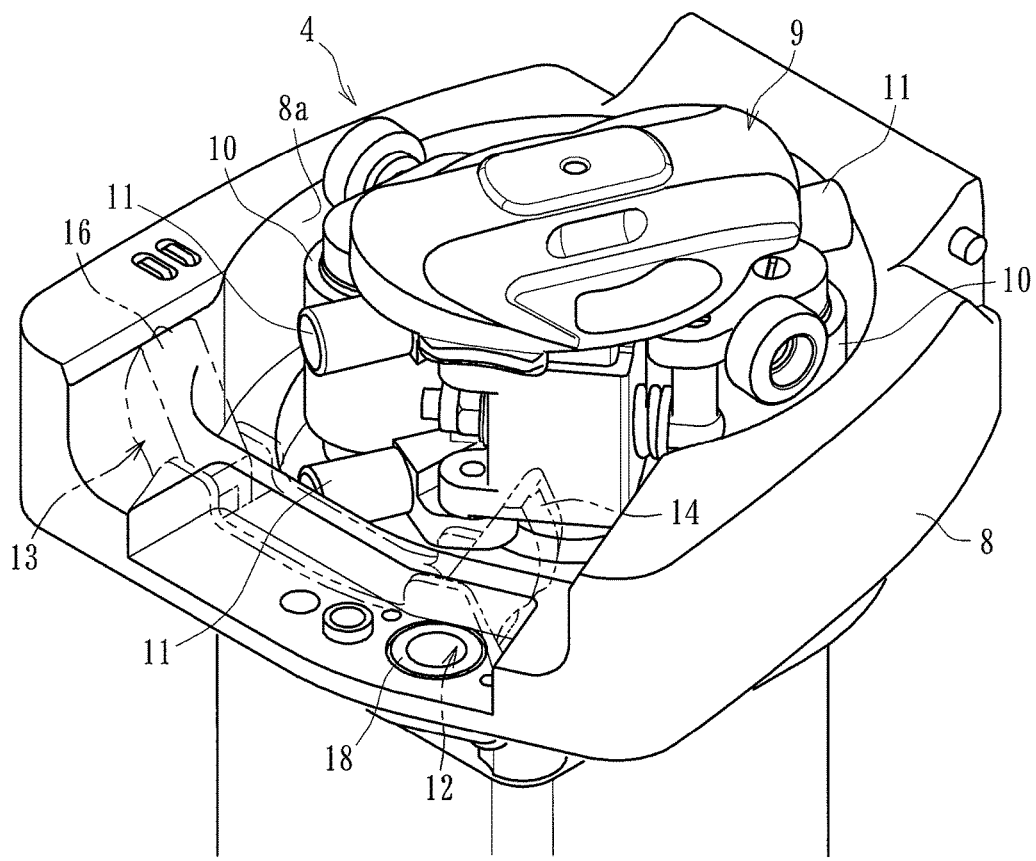

[Fig 3]
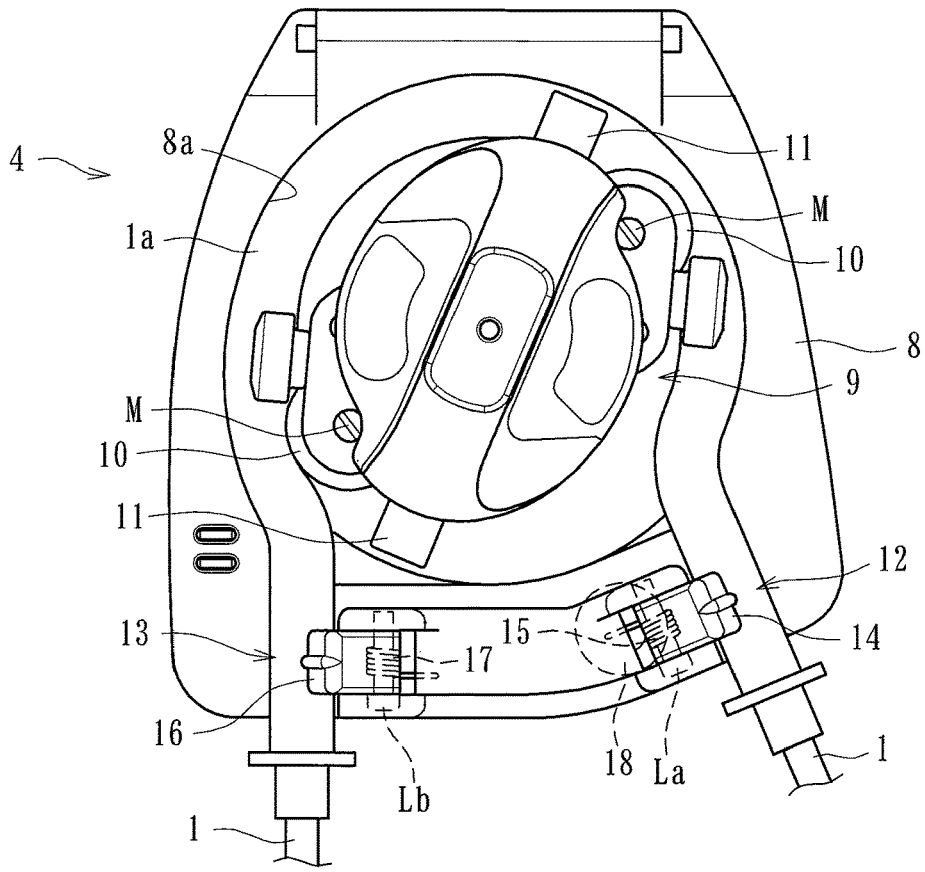
[Fig 4]
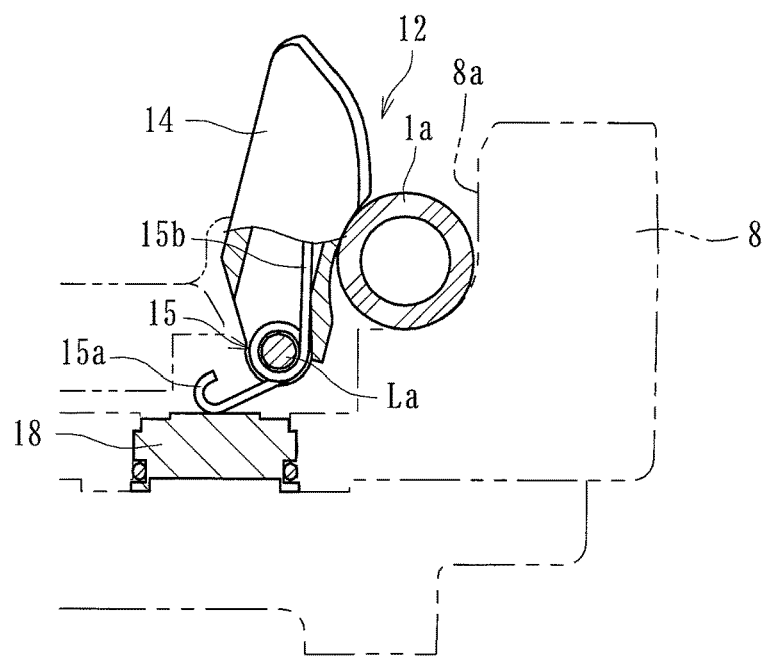

[Fig 5]
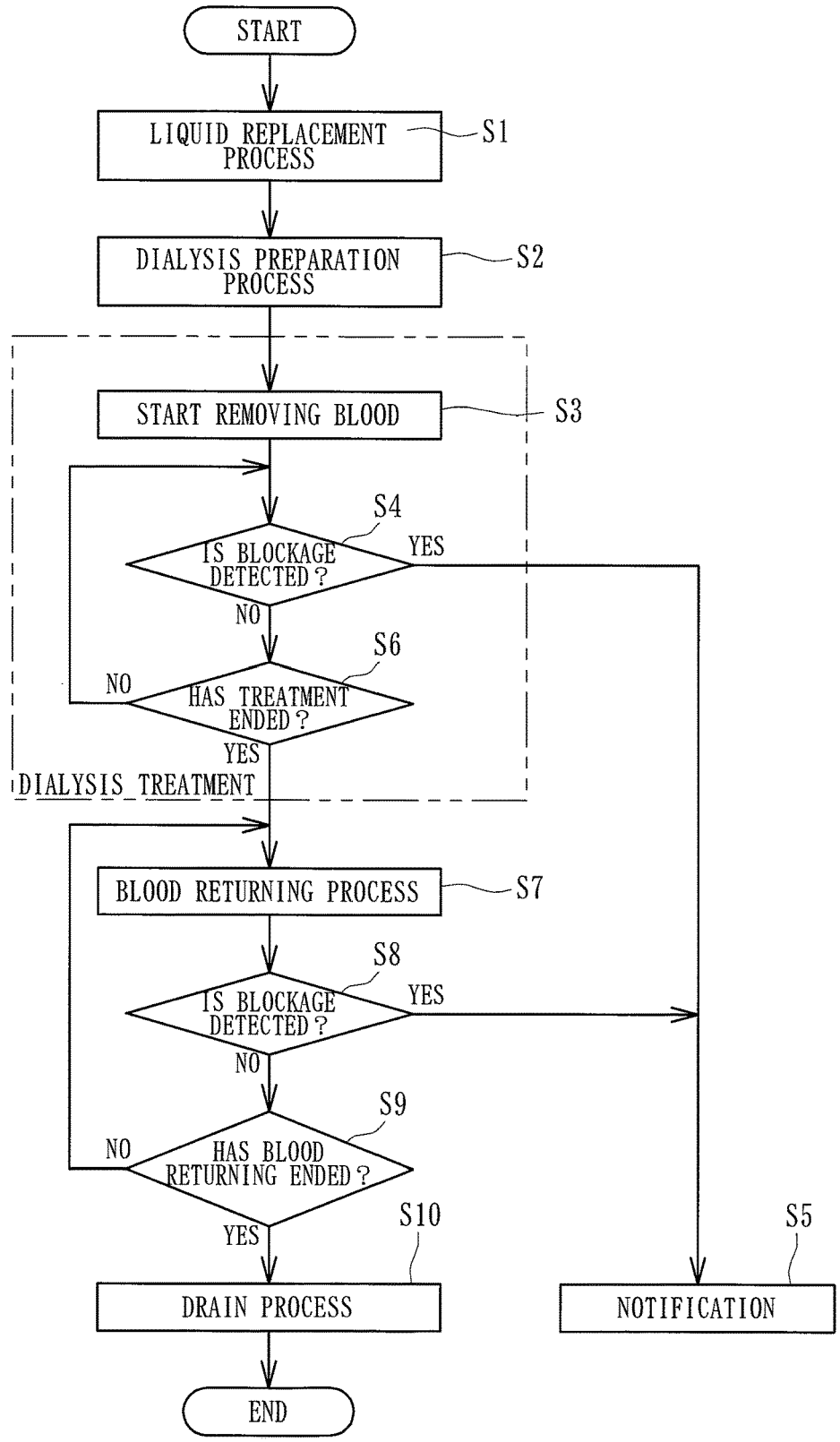

[Fig 6]
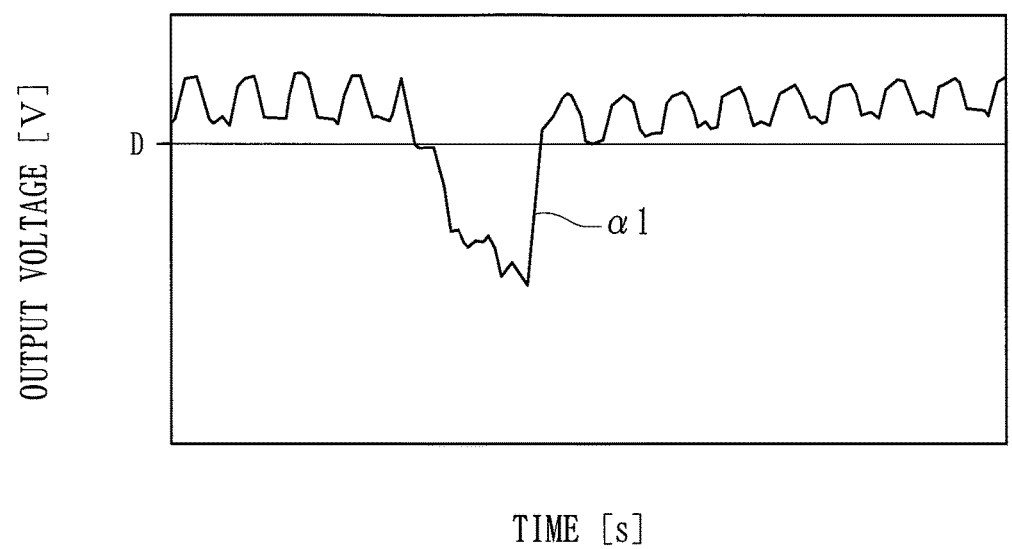

[Fig 7]
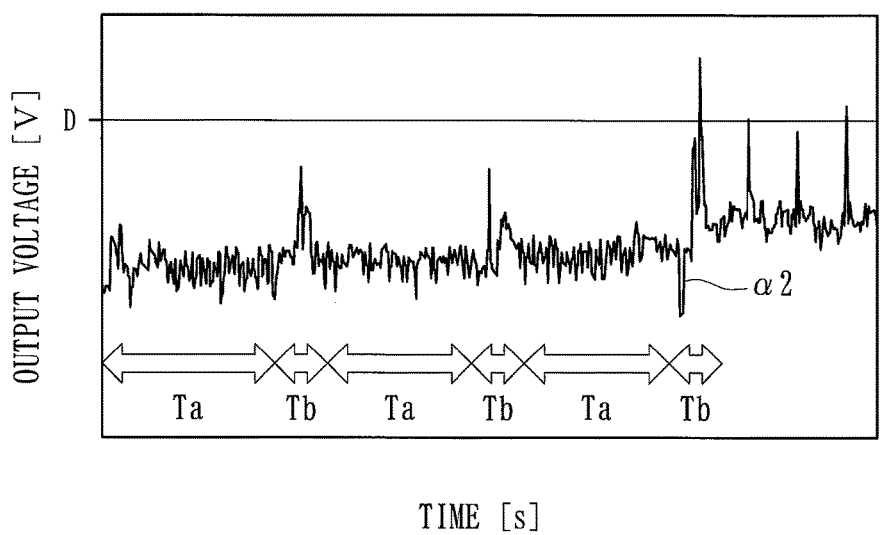
[Fig 8]
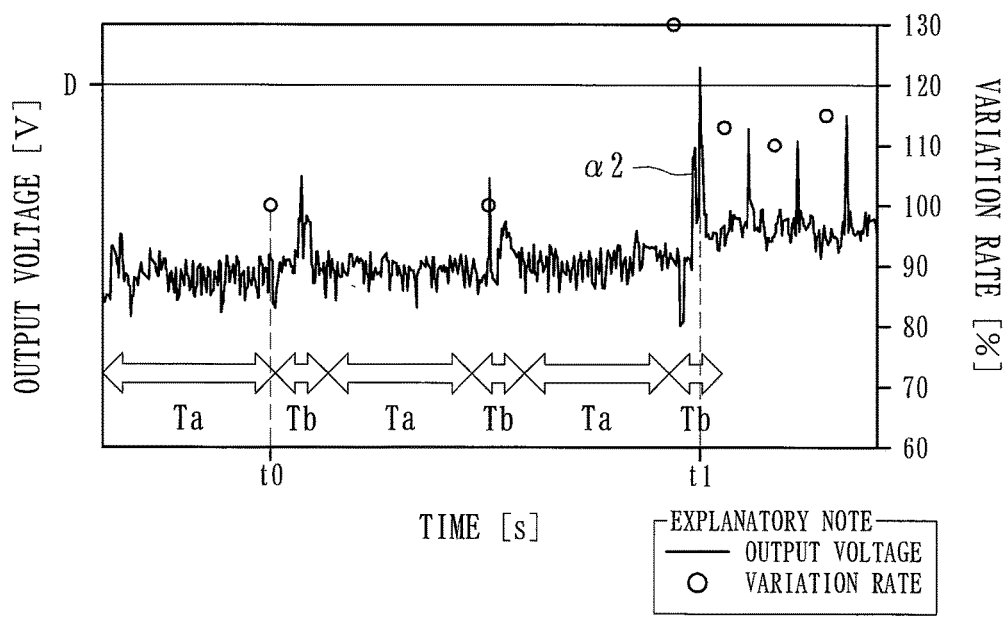

[ Fig 9 ]
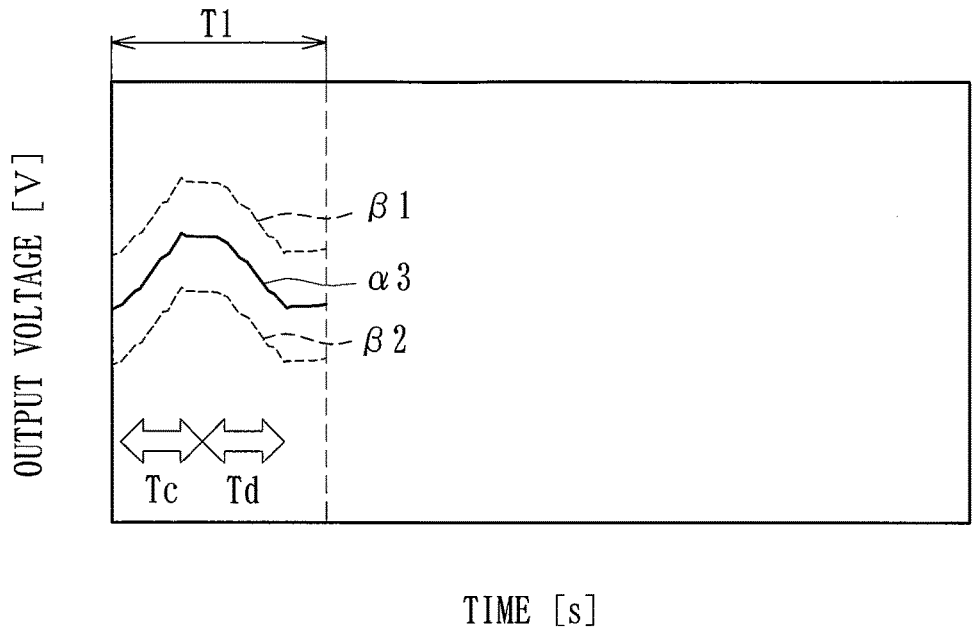
[ Fig 10 ]
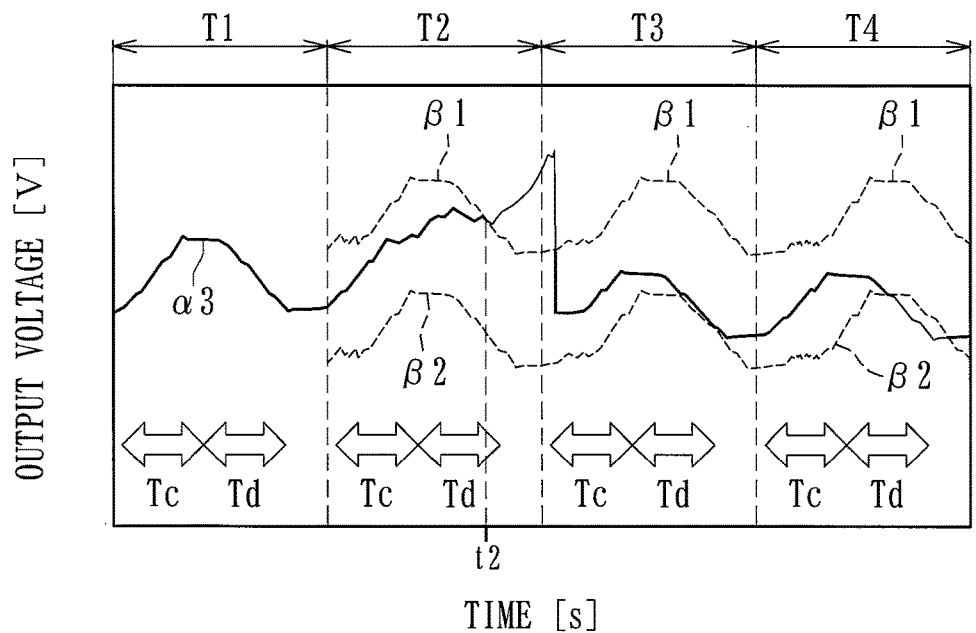

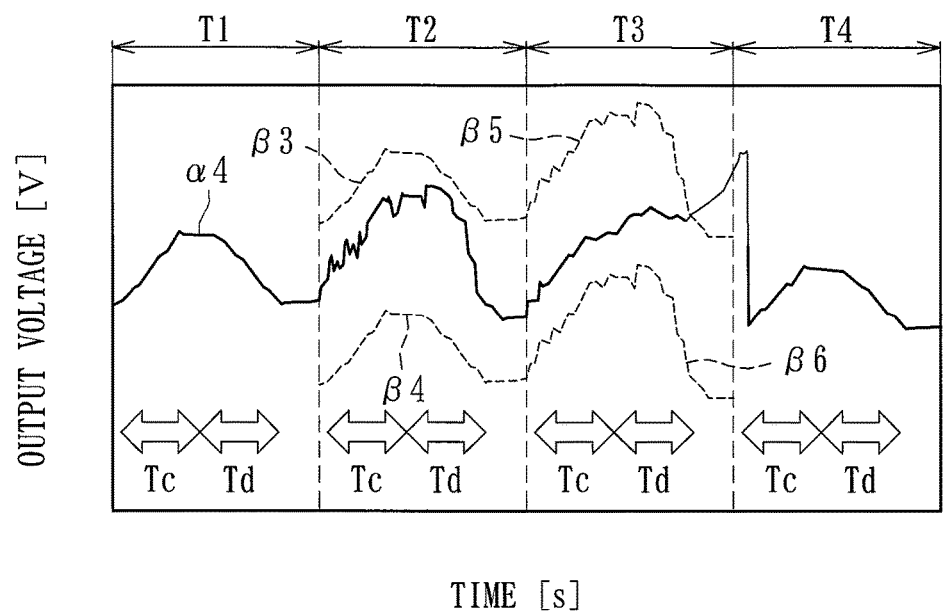
[Fig 11]

[Fig 12]
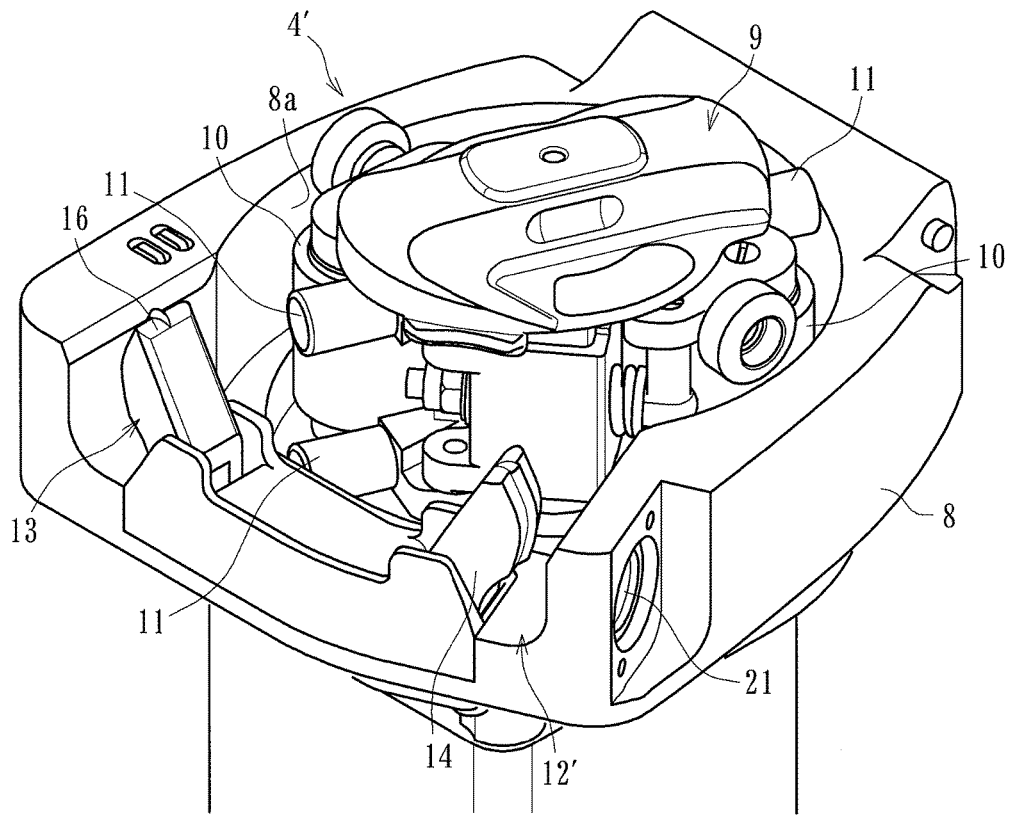
[Fig 13]
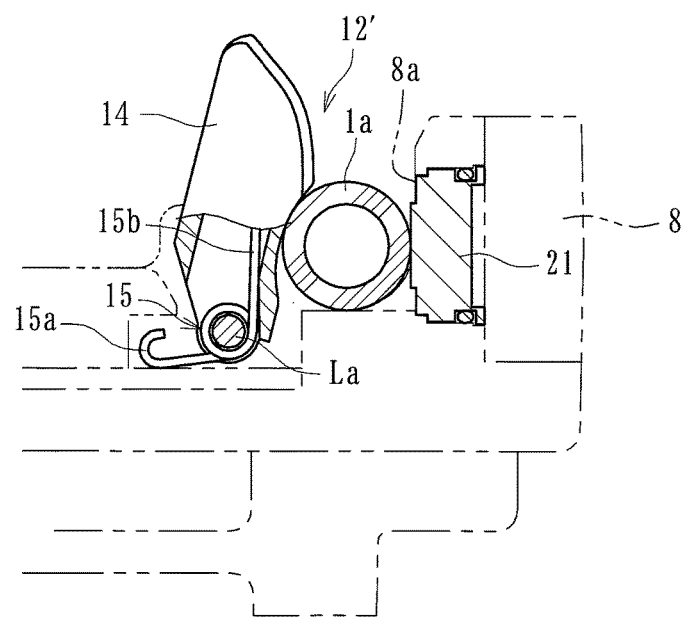

PERISTALTIC PUMP

FIELD

The present invention relates to a peristaltic pump that includes a mounting concave section on which a peristaltically-actuated tube connected to a liquid flow route, through which a predetermined liquid is circulatable, is mountable and a peristalsis section which compresses the peristaltically-actuated tube mounted on the mounting concave section in a radial direction and causes the peristaltically-actuated tube to be peristaltically actuated in a longitudinal direction such that a liquid therein is flowable in the liquid flow route.

BACKGROUND

A normal blood circuit used in a hemodialysis treatment is mainly configured to include an arterial blood circuit to which an arterial puncture needle is attached at the tip thereof and a venous blood circuit to which a venous puncture needle is attached at the tip thereof such that a blood purifier such as a dialyzer can be connected to base ends of these arterial blood circuit and venous blood circuit. In the configuration, a peristaltic blood pump is provided on the arterial blood circuit, the blood pump is caused to normally rotate in a state in which both the arterial puncture needle and the venous puncture needle are punctured into a patient, and thereby, blood is collected through the arterial puncture needle. Meanwhile, the collected blood flows in the arterial blood circuit so as to be guided to the dialyzer, then, the blood purified in the dialyzer flows into the venous blood circuit, and the blood returns into the body of the patient through the venous puncture needle such that the hemodialysis treatment is performed.

Here, as the blood pump to which the arterial blood circuit is attached, normally, the peristaltic pump is used. In the related art, the peristaltic pump is equipped with a mounting concave section on which a peristaltically-actuated tube connected to an intermediate portion of a arterial blood circuit is mountable and a peristalsis section which compresses the peristaltically-actuated tube mounted on the mounting concave section in a radial direction and causes the peristaltically-actuated tube to be peristaltically actuated in a longitudinal direction such that a liquid (priming solution, blood, or the like) therein is flowable in the arterial blood circuit (for example, see PTL 1 and PTL 2).

PTL 1: Japanese Unexamined Patent Application Publication No. 2008-425.

PTL 2: Japanese Unexamined Patent Application Publication No. 2008-2388.

SUMMARY

However, the peristaltic pump in the related art described above has problems as follows.

The arterial puncture needle is attached to the tip of the arterial blood circuit as the liquid flow route, and the blood pump as the peristaltic pump is caused to normally rotate while the arterial puncture needle is punctured into a patient, thereby, blood removing is performed, and the blood is extracorporeally circulated. During removing blood, as the tip of the arterial puncture needle is attached to a patient's vascular wall, or the like, which results in blocking the liquid flow route, there is a concern that negative pressure is produced between the arterial puncture needle and the blood pump and a flow rate of blood which is extracorporeally circulated becomes less than a preset blood flow rate.

In addition, recently, in order to achieve automatic blood returning after treatment, a blood returning method is proposed, in which the blood pump is reversely rotated (rotation drive in a direction opposite to a direction during the treatment) and, thereby, blood in the arterial blood circuit returns into the patient's body. During returning the blood, when the arterial puncture needle is clogged with the blood which returns into the patient's body, which results in blocking the liquid flow route, there is a concern that excessive pressure (in this case, positive pressure) is produced between the arterial puncture needle and the blood pump.

There is proposed a method in which a pressure detecting unit that is referred to as a so-called pillow is connected to the liquid flow route on the upstream-side (tip side of the arterial blood circuit) from a portion (a portion to which the peristaltically-actuated tube is connected) of the arterial blood circuit on which the blood pump is provided and, thereby, negative pressure during treatment and positive pressure during returning blood can be detected. The pressure detecting unit is formed of a chamber shaped member that has a predetermined capacity and is deformable, and configured to be deflated in a state in which pressure in the arterial blood circuit becomes low and to be inflated in a state in which pressure in the arterial blood circuit becomes high.

Although it is possible to grasp the imparting of the negative pressure during the blood removing and of the excessive pressure during returning blood by using the pressure detecting unit, a new separate member (pressure detecting unit) needs to be connected to the intermediate portion of the arterial blood circuit. Therefore, there is a concern that a manufacturing cost is increased, an inter-flow-routes step on a connection section between the pressure detecting unit and the arterial blood circuit is formed, and blood is stagnant at the step at the time of removing blood or returning blood.

The present invention is achieved with such problems taken into account and, thus, provides a peristaltic pump in which blockage of a liquid flow route is detected without connecting a new separate member to the liquid flow route.

Solution to Problem

The invention according to the teachings herein provides a peristaltic pump that includes a mounting concave section on which a peristaltically-actuated tube connected to a liquid flow route, through which a predetermined liquid is circulatable, is mountable; a peristalsis section which compresses the peristaltically-actuated tube mounted on the mounting concave section in a radial direction and causes the peristaltically-actuated tube to be peristaltically actuated in a longitudinal direction such that a liquid therein is flowable to the liquid flow route; displacement detecting means that is able to detect displacement of the peristaltically-actuated tube mounted on the mounting concave section in the radial direction; and blockage detecting means that is able to detect a blockage of the liquid flow route based on the displacement detected by the displacement detecting means.

The invention according to the teachings herein provides the peristaltic pump as is taught herein that further includes a rotor in which a plurality of the peristalsis sections are formed. The rotor rotates in the mounting concave section, and thereby, the peristaltically-actuated tube mounted on the mounting concave section is capable of being peristaltically actuated by the peristalsis section in a cycle, and the blockage detecting means detects a blockage of the liquid flow route, based on an output waveform obtained by a continuous detection of the displacement performed by the displacement detecting means while the rotor is rotated such that the peristaltically-actuated tube is peristaltically actuated by the peristalsis section in a cycle.

The invention according to the teachings herein provides the peristaltic pump as is taught herein in which the blockage detecting means detects a blockage of the liquid flow route based on an amplitude or a cycle of the output waveform.

The invention according to the teachings herein provides the peristaltic pump as is taught herein in which the peristaltically-actuated tube is connected to an intermediate portion of the arterial blood circuit for extracorporeally circulating blood of a patient at the time of blood purification treatment and is configured so that a blockage of the arterial blood circuit during the blood purification treatment and a blockage of the arterial blood circuit at the time of returning blood after the blood purification treatment can be detected.

The invention according to the teachings herein provides the peristaltic pump as is taught herein that further includes grasping means for grasping the peristaltically-actuated tube mounted on the mounting concave section. The displacement detecting means is able to detect displacement of a portion grasped by the grasping means in the radial direction.

The invention according to the teachings herein provides the peristaltic pump as is taught herein in which the grasping means has a grasping piece that presses the peristaltically-actuated tube in the radial direction so as to grasp the peristaltically-actuated tube and biasing means that biases the grasping piece against the peristaltically-actuated tube and the displacement detecting means detects a load applied on a fixed end side of the biasing means and detects displacement of the peristaltically-actuated tube in the radial direction based on the detected load.

The invention according to the teachings herein provides the peristaltic pump as is taught herein in which the grasping means has a grasping piece that presses the peristaltically-actuated tube in the radial direction so as to grasp the peristaltically-actuated tube and biasing means that biases the grasping piece against the peristaltically-actuated tube and the displacement detecting means is provided on a portion facing the grasping piece with the peristaltically-actuated tube interposed therebetween, detects pressure which is imparted on the side surface of the peristaltically-actuated tube pressed by the grasping piece, and detects displacement of the peristaltically-actuated tube in the radial direction based on the detected pressure.

The invention according to the teachings herein provides a blood purification apparatus including the peristaltic pump as is taught herein.

Advantageous Effects of Invention

According to the invention of the teachings herein, the displacement detecting means that is able to detect the displacement of the peristaltically-actuated tube mounted on the mounting concave section in the radial direction and the blockage detecting means that is able to detect the blockage of the liquid flow route based on the displacement detected by the displacement detecting means are provided. Therefore, it is possible to detect the blockage of the liquid flow route without connecting a new separate member to the liquid flow route.

According to the invention of the teachings herein, the blockage detecting means detects the blockage of the liquid flow route, based on an output waveform obtained by the continuous detection of the displacement performed by the displacement detecting means while the rotor is rotated such that the peristaltically-actuated tube is peristaltically actuated by the peristalsis section in a cycle. Therefore, it is possible to detect the blockage of the liquid flow route smoothly and with higher accuracy.

According to the invention of the teachings herein, the blockage detecting means detects the blockage of the liquid flow route based on the amplitude or the cycle of the output waveform. Therefore, it is possible to detect the blockage of the liquid flow route simply and with higher accuracy.

According to the invention of the teachings herein, the peristaltically-actuated tube is connected to the intermediate portion of the arterial blood circuit for extracorporeally circulating blood of a patient at the time of the blood purification treatment and is configured such that the blockage of the arterial blood circuit during the blood purification treatment and the blockage of the arterial blood circuit at the time of returning blood after the blood purification treatment can be detected. Therefore, it is possible to detect negative pressure produced by the blockage of the arterial blood circuit at the time of removing blood and positive pressure produced by the blockage of the arterial blood circuit at the time of returning blood.

According to the invention of the teachings herein, the grasping means for grasping the peristaltically-actuated tube mounted on the mounting concave section is provided and the displacement detecting means is able to detect displacement of a portion grasped by the grasping means in the radial direction. Therefore, the peristaltically-actuated tube mounted on the mounting concave section is grasped by the grasping means and, thereby, it is possible to detect the displacement by the displacement detecting means and the blockage of the liquid flow route such that it is possible to lower a work burden on medical staff or the like.

According to the invention of the teachings herein, the grasping means has the grasping piece that presses the peristaltically-actuated tube in the radial direction so as to grasp the peristaltically-actuated tube and the biasing means that biases the grasping piece against the peristaltically-actuated tube and the displacement detecting means detects the load applied on the fixed end side of the biasing means and detects the displacement of the peristaltically-actuated tube in the radial direction based on the detected load. Therefore, it is possible for the peristaltic pump to fulfill both a function of enabling the biasing means to generate a grasping force with respect to the peristaltically-actuated tube and a function of detecting the displacement of the peristaltically-actuated tube in the radial direction by the displacement detecting means.

According to the invention of the teachings herein, the grasping means has the grasping piece that presses the peristaltically-actuated tube in the radial direction so as to grasp the peristaltically-actuated tube and the biasing means that biases the grasping piece against the peristaltically-actuated tube and the displacement detecting means is provided on the portion facing the grasping piece with the peristaltically-actuated tube interposed therebetween, detects pressure which is imparted on the side surface of the peristaltically-actuated tube pressed by the grasping piece, and detects displacement of the peristaltically-actuated tube in the radial direction based on the detected pressure. Therefore, it is possible for the peristaltic pump to fulfill both a function of enabling the displacement detecting means to receive a pressing force against the peristaltically-actuated tube and a function of detecting the displacement of the peristaltically-actuated tube in the radial direction.

According to the invention of the teachings herein, it is possible to provide a blood purification apparatus including the peristaltic pump according any of the teachings herein.

BRIEF DESCRIPTION OF DRAWINGS

FIG. 1 is a diagram schematically illustrating a blood circuit to which a blood pump is applied as a peristaltic pump according to an embodiment of the present invention.

FIG. 2 is a perspective view illustrating the blood pump.

FIG. 3 is a plan view illustrating the blood pump.

FIG. 4 is a schematic cross-sectional view illustrating displacement detecting means provided on the blood pump.

FIG. 5 is a flowchart illustrating control details of a blood purification apparatus to which the blood pump is applied.

FIG. 6 is a graph illustrating an output waveform obtained through continuously performing detection of displacement by the displacement detecting means of the blood pump at the time of removing blood.

FIG. 7 is a graph illustrating an output waveform obtained through continuously performing detection of displacement by the displacement detecting means of the blood pump at the time of returning blood.

FIG. 8 is a graph illustrating an output waveform and a variation rate obtained through continuously performing detection of displacement by the displacement detecting means of the blood pump at the time of returning blood.

FIG. 9 is a graph for illustrating a method (method performed by fixing a vertical warning range) of detecting a blockage of a liquid flow route based on an output waveform obtained through continuously performing detection of displacement by the displacement detecting means of the blood pump at the time of returning blood.

FIG. 10 is a graph for illustrating a method (method performed by fixing a vertical warning range) of detecting a blockage of a liquid flow route based on an output waveform obtained through continuously performing detection of displacement by the displacement detecting means of the blood pump at the time of returning blood.

FIG. 11 is a graph for illustrating a method (method performed by changing a vertical warning range) of detecting a blockage of a liquid flow route based on an output waveform obtained through continuously performing detection of displacement by the displacement detecting means of the blood pump at the time of returning blood.

FIG. 12 is a perspective view illustrating a blood pump as a peristaltic pump according to another embodiment of the present invention.

FIG. 13 is a schematic cross-sectional view illustrating displacement detecting means provided on the blood pump.

DETAILED DESCRIPTION

Hereinafter, an embodiment of the present invention will be specifically described with reference to the drawings. The present application claims priority to Japanese Application No. 2012-231968 filed on Oct. 19, 2012 and International Application No. PCT/JP2013/078272, filed on Oct. 18, 2013, the contents of both are incorporated by reference herein in their entirety for all purposes.

A peristaltic pump according to the present embodiment is formed of a blood pump that is provided on a blood circuit (specifically, an arterial blood circuit) for performing a blood purification treatment (for example, a hemodialysis treatment) by extracorporeally circulating blood of a patient. As illustrated in FIG. 1, the blood circuit, to which the peristaltic pump is applied, is mainly configured to have an arterial blood circuit 1, a venous blood circuit 2, and a dialyzer 3 as a blood purifier. The arterial blood circuit 1 corresponds to "a liquid flow route to which a peristaltically-actuated tube 1a is connected", according to the present invention.

The arterial blood circuit 1 configures the liquid flow route that is formed of a flexible tube through which a predetermined liquid can circulate such that an arterial puncture needle a can be attached to the tip thereof through a connector c and an arterial air trap chamber 5 for removing bubbles is connected to an intermediate portion thereof. A physiological saline solution supplying line L3 is connected to the arterial blood circuit 1 through a T shape tube T and containing means 7 that is referred to as a saline bag is connected to a tip of the physiological saline solution supplying line L3. The physiological saline solution supplying line L3 is configured to be arbitrarily openable and closable by valve means (not illustrated) that is formed of an electromagnetic valve, forceps, or the like and to be able to supply the physiological saline solution in the containing means 7 into the blood circuit by switching the valve means to an opening state.

In addition, the peristaltically-actuated tube 1a is connected to the intermediate portion (between the T shape tube T and the arterial air trap chamber 5) of the arterial blood circuit 1 and it is possible to mount the peristaltically-actuated tube 1a on the blood pump 4 (specifically, a mounting concave section 8a in a stator 8 of the blood pump 4 to be described later in detail). The peristaltically-actuated tube 1a is compressed in the radial direction by a roller 10 (peristalsis section) of the blood pump 4 (peristaltic pump) and is be peristaltically actuated in the longitudinal direction such that a liquid therein can flow in a rotating direction of the rotor 9 and is formed of a flexible tube which is more flexible and has a greater diameter than other flexible tubes which configure the arterial blood circuit 1.

The venous blood circuit 2 configures the liquid flow route that is formed of a flexible tube through which a predetermined liquid can circulate such that a venous puncture needle b can be attached to the tip thereof through a connector d and a venous air trap chamber 6 for removing bubbles is connected to an intermediate portion thereof. A flexible tube configuring the venous blood circuit 2 has substantially the same material and size of a diameter as the flexible tube configuring the arterial blood circuit 1. The dialyzer 3 for purifying blood is connected between the arterial blood circuit 1 and the venous blood circuit 2.

The dialyzer 3 is formed of multiple hollow fibers therein, in which minute holes (pores) are formed, in a casing section, a blood guiding-in port 3a, a blood guiding-out port 3b, a dialysate guiding-in port 3c, and a dialysate guiding-out port 3d are formed, and base ends of the arterial blood circuit 1 and the venous blood circuit 2 are connected to the blood guiding-in port 3a and the blood guiding-out port 3b, respectively. In addition, the dialysate guiding-in port 3c and the dialysate guiding-out port 3d are connected, respectively, to a dialysate guiding-in line L1 and a dialysate guiding-out line L2 which extend from a dialysis apparatus main body (not illustrated).

Blood of a patient guided into the dialyzer 3 passes inside a hollow fiber membrane (blood flow route) in the dialyzer 3, and then is discharged from the blood guiding-out port 3b. Dialysate guided into the dialyzer 3 through the dialysate guiding-in port 3c passes outside a hollow fiber membrane (dialysate flow route), and then is discharged from the dialysate guiding-out port 3d. Accordingly, waste in the blood that passes through the blood flow route is caused to pass through on the dialysate side, can be purified, and it is possible for the purified blood to return into the body of the patient through the venous blood circuit 2. In this way, blood collected from the arterial puncture needle a is purified by the dialyzer 3 in a course of the extracorporeal circulation through the arterial blood circuit 1 and the venous blood circuit 2.

Here, as illustrated in FIGS. 2 to 4, the blood pump 4 according to the present embodiment is mainly configured to have the stator 8, the rotor 9 that is rotatable in the stator 8, the roller 10 (peristalsis section) formed in the rotor 9, a pair of upper and lower guide pins 11, upstream-side grasping means 12, downstream-side grasping means 13, and a load sensor 18 as the displacement detecting means. In the same drawings, a cover that covers the upper section of the stator 8 in the blood pump 4 is omitted.

The mounting concave section 8a, on which the peristaltically-actuated tube 1a is mounted, is formed in the stator 8. The stator 8 is configured to mount the peristaltically-actuated tube 1a along an inner circumferential wall surface which forms the mounting concave section 8a as illustrated in FIGS. 3 and 4. In addition, the rotor 9 that is rotatable by a motor is provided substantially at the center of the mounting concave section 8a. A pair of (two) rollers 10 and the guide pins 11 are provided on the side surface (surface facing the inner circumferential wall surface of the mounting concave section 8a) of the rotor 9.

The roller 10 is rotatable about a rotating shaft M formed on the outer edge side of the rotor 9 such that the roller 10 compresses the peristaltically-actuated tube 1a mounted on the mounting concave section 8a in the radial direction and causes the peristaltically-actuated tube 1a to be peristaltically actuated in the longitudinal direction (flowing direction of the blood) along with the rotation of the rotor 9 and, thereby, can cause the blood to flow in the arterial blood circuit 1. That is, when the peristaltically-actuated tube 1a is mounted on the mounting concave section 8a and the rotor 9 is rotated, the peristaltically-actuated tube 1a is compressed between the roller 10 and the inner circumferential wall surface of the mounting concave section 8a and the peristalsis can be performed in the rotating direction (longitudinal direction) along with the rotation of the rotor 9. Since the peristalsis causes the blood in the arterial blood circuit 1 to flow in the rotating direction of the rotor 9, it is possible to extracorporeally circulate the blood through the arterial blood circuit 1.

As illustrated in FIG. 2, the guide pins 11 are formed of a pair of upper and lower pin-like members which are formed to protrude toward the inner circumferential wall surface of the mounting concave section 8a from the upper end side and the lower end side of the rotor 9 and the peristaltically-actuated tube 1a is held between these pair of upper and lower guide pins 11. That is, the peristaltically-actuated tube 1a is held at a normal position by the pair of upper and lower guide pins 11 at the time of rotating of the rotor 9 and the peristaltically-actuated tube a is not separated upward from the mounting concave section 8a by the upside guide pin 11.

The upstream-side grasping means 12 is used for grasping the upstream side (a portion to which the tip side of the arterial blood circuit 1 is connected) of the peristaltically-actuated tube 1a that is mounted on the mounting concave section 8a of the stator 8 in the blood pump 4. As illustrated in FIGS. 2 to 4, the upstream-side grasping means 12 has a grasping piece 14 that presses the peristaltically-actuated tube 1a in the radial direction so as to grasp the peristaltically-actuated tube 1a and a torsion spring 15 (biasing means) which biases the grasping piece 14 against the peristaltically-actuated tube 1a.

As illustrated in FIG. 4, the grasping piece 14 is formed of components that are swingable about a swinging shaft La such that the grasping piece 14 is biased by the torsion spring 15 in a direction of grasping with a relatively strong force, presses a portion of the peristaltically-actuated tube 1a on the upstream side so as to fix and interpose the peristaltically-actuated tube 1a, and thereby, can be fixed. As illustrated in the same drawing, the torsion spring 15 is mounted on the swinging shaft La so as to bias the grasping piece 14 and has a fixed end 15a positioned at a fixed section of the stator 8 (according to the present embodiment, the load sensor 18 mounted on the stator 8) and a pressing end 15b that presses the grasping piece 14. Instead of the torsion spring 15, another biasing means that biases the grasping piece 14 may be used.

The downstream-side grasping means 13 is used for grasping the downstream side (a portion to which the base end side of the arterial blood circuit 1 is connected) of the peristaltically-actuated tube a that is mounted on the mounting concave section 8a of the stator 8 in the blood pump 4. The downstream-side grasping means 13 has a grasping piece 16 that presses the peristaltically-actuated tube 1a in the radial direction so as to grasp the peristaltically-actuated tube 1a and a torsion spring 17 which biases the grasping piece 16 against the peristaltically-actuated tube 1a.

The grasping piece 16 is formed of components that are swingable about a swinging shaft Lb such that similar to the grasping piece 14 of the upstream-side grasping means 12, the grasping piece 16 is biased by the torsion spring 17 in a direction of grasping with a relatively strong force, presses a portion of the peristaltically-actuated tube 1a on the downstream side so as to fix and interpose the peristaltically-actuated tube 1a, and thereby, can be fixed. Similar to the torsion spring 15 of the upstream-side grasping means 12, the torsion spring 17 is mounted on the swinging shaft Lb so as to bias the grasping piece 16 and has a fixed end positioned at a fixed section of the stator 8 and a pressing end that presses the grasping piece 16.

The load sensor 18 as the displacement detecting means can detect displacement of a portion of the peristaltically-actuated tube 1a which is grasped by the upstream-side grasping means 12 in the radial direction. Therefore, according to the present embodiment, a load applied on the fixed end 15a side of the torsion spring 15 (biasing means) is detected and the displacement of the peristaltically-actuated tube 1a in the radial direction is detected based on the detected load. The load sensor 18 can generate an electrical signal in accordance with the applied load.

As illustrated in FIG. 1, blockage detecting means 19 is electrically connected to the load sensor 18 as the displacement detecting means. The blockage detecting means 19 is configured of a microcomputer or the like mounted on a dialysis apparatus main body or provided separately from the dialysis apparatus main body such that the blockage detecting means 19 can perform predetermined control (control for performing computation or the like so as to detect a blockage of the liquid flow route) based on the displacement of the peristaltically-actuated tube 1a in the radial direction which is detected by the load sensor 18.

To be more specific, the blockage detecting means 19 can detect a blockage of the arterial blood circuit 1 (liquid flow route) based on the displacement detected by the load sensor

18 (displacement detecting means) and, according to the present embodiment, is configured to detect the blockage of the liquid flow route, based on the output waveform obtained by a continuous detection of the displacement performed by the load sensor 18 (displacement detecting means) while the rotor 9 is rotated in the mounting concave section 8a such that the peristaltically-actuated tube 1a is peristaltically actuated by the roller 10 (peristalsis section) in a cycle.

For example, at the time of removing blood in the blood purification treatment, while the blood pump 4 is caused to normally rotate (rotation to the left in FIG. 1), the load sensor 18 (displacement detecting means) is caused to continuously detect the displacement. In this way, as illustrated in FIG. 6, an output waveform $\alpha 1$ is obtained with the vertical axis as the output voltage (V) and with the horizontal axis as time (s), and amplitude and a cycle in the output waveform $\alpha 1$ are monitored by the blockage detecting means 19.

An attachment of the tip of the arterial puncture needle a on a vascular wall of a patient or the like causes the arterial blood circuit 1 to be blocked. When negative pressure is produced in a portion of the arterial blood circuit 1 between the tip of the arterial blood circuit 1 and the peristaltically-actuated tube 1a due to the blockage, the amplitude of the output waveform $\alpha 1$ sharply changes (specifically, the output voltage is steeply dropped and exceeds a predetermined threshold value D) and a phenomenon, in which a cyclic nature is disturbed, occurs, as illustrated in the same drawing.

Further, the blockage detecting means 19 is configured to detect a phenomenon (the amplitude of the output waveform $\alpha 1$ exceeds the predetermined threshold value D or the cyclic nature of the output waveform $\alpha 1$ is disturbed) which occurs due to the blockage of the arterial blood circuit 1 such that the detection of the blockage of the arterial blood circuit 1 (liquid flow route) is performed based on the amplitude or the cycle of the output waveform $\alpha 1$. According to the present embodiment, when the condition that the amplitude of the output waveform $\alpha 1$ exceeds the predetermined threshold value D is fulfilled, the detection of the blockage of the arterial blood circuit 1 (liquid flow route) is performed; however, the disturbance of the cyclic nature of the output waveform $\alpha 1$ may be detected such that the detection of the blockage of the arterial blood circuit 1 (liquid flow route) is performed. For example, a reference output waveform obtained in a state, in which the arterial blood circuit 1 is not blocked, is stored and the reference output waveform and the output waveform obtained at the time of removing blood are compared to each other with time. In this way, it is possible to detect the disturbance of the cyclic nature.

In addition, according to the present embodiment, for example, at the time of returning blood after the blood purification treatment while the blood pump 4 is caused to repeat normal rotation (rotation to the left in FIG. 1) and reverse rotation (rotation to the right in FIG. 1) alternately, the detection of the displacement is continuously performed by the load sensor 18 (displacement detecting means). In this way, as illustrated in FIG. 7, an output waveform $\alpha 2$ is obtained with the vertical axis as the output voltage (V) and the horizontal axis as time (s), and the variation of the output voltage in the output waveform $\alpha 2$ is monitored by the blockage detecting means 19.

To be more specific, according to the present embodiment, there are provided both a venous blood returning process Ta of returning blood on the venous blood circuit 2 side (to be more exact, as illustrated in FIG. 1, a flow route from a connection portion of the arterial blood circuit 1 with the physiological saline solution supplying line L3 to a connection portion of the arterial blood circuit 1 with the dialyzer 3, a blood flow route in the dialyzer 3, and a flow route in the venous blood circuit 2) into the patient by the normal rotation of the blood pump 4 and an arterial blood returning process Tb of returning blood on the arterial blood circuit 1 side (to be more exact, as illustrated in FIG. 1, a flow route from a connection portion of the arterial blood circuit 1 with the physiological saline solution supplying line L3 to the tip of the arterial blood circuit 1) into the patient by the reverse rotation of the blood pump 4. In the embodiment, the venous blood returning process Ta and the arterial blood returning process Tb are performed alternately.

When the tip of the arterial puncture needle a is clogged with thrombi which results in the blockage of the arterial blood circuit 1 and thereby, the positive pressure is produced at a portion of the arterial blood circuit 1 between the tip of the arterial blood circuit 1 and the peristaltically-actuated tube 1a, the amplitude of the output waveform $\alpha 2$ sharply changes (specifically, the output voltage is steeply increased and exceeds a predetermined threshold value D) and a phenomenon, in which a cyclic nature is disturbed, occurs, as illustrated in the same drawing.

Further, the blockage detecting means 19 is configured to detect a phenomenon (the amplitude of the output waveform $\alpha 2$ exceeds the predetermined threshold value D or the cyclic nature of the output waveform $\alpha 2$ is disturbed) which occurs due to the blockage of the arterial blood circuit 1 such that the detection of the blockage of the arterial blood circuit 1 (liquid flow route) is performed based on the amplitude or the cycle of the output waveform $\alpha 2$. According to the present embodiment, when the condition that the amplitude of the output waveform $\alpha 2$ exceeds the predetermined threshold value D is fulfilled, the detection of the blockage of the arterial blood circuit 1 (liquid flow route) is performed; however, the disturbance of the cyclic nature of the output waveform $\alpha 2$ may be detected such that the detection of the blockage of the arterial blood circuit 1 (liquid flow route) is performed. For example, a reference output waveform obtained in a state in which the arterial blood circuit 1 is not blocked is stored and the reference output waveform and the output waveform obtained at the time of removing blood are compared to each other with time. In this way, it is possible to detect the disturbance of the cyclic nature.

Further, for example, at the time of returning blood after the blood purification treatment, similar to the venous blood returning process Ta and the arterial blood returning process Tb described above, while the blood pump 4 is caused to repeat normal rotation and reverse rotation alternately, the detection of the displacement is continuously performed by the load sensor 18 (displacement detecting means). In this way, as illustrated in FIG. 8, a configuration may be employed, in which an output waveform $\alpha 2$ is obtained with the vertical axis as the output voltage (V) and the horizontal axis as time (s), and the variation rate of the output voltage in the output waveform $\alpha 2$ is monitored by the blockage detecting means 19.

In this case, as illustrated in FIG. 8, the output voltage at a predetermined time t0 is set to the reference voltage (100%) and a variation rate from the reference voltage is sequentially detected by the blockage detecting means 19 so as to be monitored. When the condition that the blockage detecting means 19 detects that the variation rate exceeds the predetermined threshold value D (120% according to the present embodiment) is fulfilled, it is possible to determine that the arterial blood circuit 1 (liquid flow route) is blocked.

In FIG. 8, since the variation rate exceeds the predetermined threshold value D at a time t1, the blockage of the arterial blood circuit 1 is detected at the time point.

Further, for example, at the time of returning blood after the blood purification treatment (according to the present embodiment, at the time of returning blood through the arterial blood circuit 1), while the blood pump 4 is caused to repeat normal rotation and reverse rotation alternately, the detection of the displacement is continuously performed by the load sensor 18 (displacement detecting means). In this way, as illustrated in FIG. 9, a waveform (reference waveform) of the first cycle T1 of an output waveform α3 may be obtained and stored and a waveform β1 which is obtained by connecting values of the output voltages which are higher than that of the reference waveform by a predetermined value and a waveform β2 which is obtained by connecting values of the output voltages which are lower than that of the reference waveform by a predetermined value may be set such that the blockage of the arterial blood circuit 1 (liquid flow route) is detected.

To be more specific, according to the present embodiment, when returning blood through the arterial blood circuit 1 after returning blood on the venous blood circuit 2 side (to be more exact, as illustrated in FIG. 1, a flow route from the connection portion of the arterial blood circuit 1 with the physiological saline solution supplying line L3 to a connection portion of the arterial blood circuit 1 with the dialyzer 3, a blood flow route in the dialyzer 3, and a flow route in the venous blood circuit 2) into the patient by the normal rotation of the blood pump 4, a pressure accumulating process Tc and a blood returning process Td are repeated so as to be performed alternately as illustrated in FIG. 9.

In the pressure accumulating process Tc, while the tip of the arterial blood circuit 1 and the tip of the venous blood circuit 2 are blocked using an electromagnetic valve or the like, the blood pump 4 is caused to normally rotate, and the pressure accumulation of physiological saline solution supplied from the physiological saline solution supplying line L3 is performed. That is, when the tips of the arterial blood circuit 1 and the venous blood circuit 2, respectively, are blocked and the normal rotation of the blood pump 4 is performed, the physiological saline solution supplied from the physiological saline solution supplying line L3 is guided to the flow route on the blood pump 4 side from the connection portion of the arterial blood circuit 1 with the physiological saline solution supplying line L3 and pressure in the flow route is accumulated.

In the blood returning process Td, in a state in which the tip of the arterial blood circuit 1 is opened while the tip of the venous blood circuit 2 is blocked, the blood pump 4 is caused to rotate reversely, thereby, the physiological saline solution of which pressure is accumulated in the pressure accumulating process Tc is caused to flow to the tip of the arterial blood circuit 1 and thus, the blood can return into the body of the patient. According to the present embodiment, the pressure accumulating process Tc and the blood returning process Td are repeated so as to be performed alternately such that it is possible to perform the blood returning on the arterial blood circuit 1 side favorably.

Even in this case, the detection of the displacement is continuously performed by the load sensor 18 (displacement detecting means), as illustrated in FIG. 10, the waveform β1 and the waveform β2 with respect to cycles T2 to T4 after the first cycle T1 are sequentially set, and the variation of the output voltage of the obtained output waveform α3 is monitored by the blockage detecting means 19. That is, the blockage detecting means 19 monitors whether or not the output waveform α3 changes in a range between the waveform β1 and the waveform β2 and it is determined that the arterial blood circuit 1 (liquid flow route) is blocked when the condition that the output waveform α3 exceeds either the waveform β1 or the waveform β2 is fulfilled. In FIG. 10, since the output waveform α3 exceeds the waveform β1 at the time t2, at the time, the blockage of the arterial blood circuit 1 is detected.

Further, according to the above description, the waveform β1 and the waveform β2 with respect to cycles T2 to T4 after the first cycle T1 are sequentially set; however, as illustrated in FIG. 11, upper and lower waveforms may be sequentially updated based on the output waveform (L4 of the previous cycle (for example, the cycle T1 for the cycle T2 and cycle T3 for the cycle T2). For example, in the cycle T2, the output waveform α4 of the cycle T1 is set to the reference waveform, a waveform β3 obtained by connecting values of the output voltages which are higher than that of the reference waveform by a predetermined value and a waveform β4 obtained by connecting values of the output voltages which are lower than that of the reference waveform by a predetermined value are set and thereby, monitoring similar to the above description is performed.

Then, in the cycle T3, the output waveform of the cycle T2 is set to the reference waveform (that is, the reference waveform is updated to that of the previous cycle) and a waveform β5 obtained by connecting values of the output voltages which are higher than that of the reference waveform by a predetermined value and a waveform β6 obtained by connecting values of the output voltages which are lower than that of the reference waveform by a predetermined value are set. The blockage detecting means 19 monitors whether or not the output waveform α4 changes in a range between the waveform β5 and the waveform β6 and it is determined that the arterial blood circuit 1 (liquid flow route) is blocked when the condition that the output waveform α4 exceeds either the waveform β5 or the waveform β6 is fulfilled.

According to the present embodiment, a notification means 20 electrically connected to the blockage detecting means 19 is provided. The notification means 20 is formed of a display means (LCD), a speaker, an external indicating lamp, or the like disposed on, for example, the dialysis apparatus main body such that the notification means 20 can notify (display on the display means, output of warning from the speaker, light-on or light-off of the external indicating lamp, or the like) medical staff or the like around, when the blockage detecting means 19 detects the blockage of the arterial blood circuit 1 (liquid flow route).

Next, control details of the blood pump 4 (peristaltic pump) according to the present embodiment will be described based on a flowchart in FIG. 5.

Before starting the dialysis treatment (blood purification treatment), first, a liquid replacement process S1 is performed, the inside of the tube in the dialysis apparatus main body is filled with dialysate, and a self-examination such as a tube leakage examination or other test is performed. Then, the process proceeds to a dialysis preparation process S2, a dialysis condition is set, the peristaltically-actuated tube 1a is mounted on the blood pump 4 in the arterial blood circuit 1, a type of peristaltically-actuated tube 1a (large-diameter tube or small-diameter tube) that is mounted is set, and priming of the blood circuit or the substitution circuit (operation of filling with substitution solution) is performed. In parallel with the dialysis preparation process S2, the priming (gas purge) on the dialysate flow route side of the dialyzer 3 is also performed.

After the dialysis preparation process S2 ends, the dialysis treatment is performed on the patient. In the dialysis treatment, the arterial puncture needle a and the venous puncture needle b are punctured into a patient, the normal rotation of the blood pump 4 causes the rotor 9 to rotate in the left direction in FIG. 1, thus the blood removing by the roller 10 (peristalsis section) starts (start of blood removing S3), and the blood of the patient extracorporeally circulates through the arterial blood circuit 1 and the venous blood circuit 2. Accordingly, the blood being subjected to the extracorporeally circulating process is purified in the dialyzer 3 and the dialysis treatment (blood purification treatment) is performed.

In the extracorporeally circulating process of blood after starting the blood removing, it is determined whether or not the blockage detecting means 19 detects the blockage of the arterial blood circuit 1 (liquid flow route) based on the displacement detected by the load sensor 18 (S4). The detection of the blockage of the arterial blood circuit 1 (liquid flow route) by the blockage detecting means 19 during the dialysis treatment is as above. When the blockage of the arterial blood circuit 1 is detected in S4, the process proceeds to S5 and notification is performed by the notification means 20 and urging the medical staff or the like to take action is performed.

In a case where it is determined that the blockage of the arterial blood circuit 1 is not detected in S4, the process proceeds to S6, and it is determined whether or not the dialysis treatment is ended. In S6, when it is determined that the dialysis treatment is not ended, the process returns to S4 and the dialysis treatment and the detection of the blockage of the arterial blood circuit 1 are continuously performed. On the other hand, when it is determined that the dialysis treatment is ended in S6, the process proceeds to S7 and a blood returning process S7 (process of returning blood in the blood circuit into the body of the patient) is performed.

In the blood returning process S7, while the arterial puncture needle a and the venous puncture needle b are punctured into the patient, the reverse rotation of the blood pump 4 causes the rotor 9 to rotate to the right direction in FIG. 1 (causes the roller 10 (peristalsis section) to rotate in the same direction). The dialysate is subjected to back-filtration from the outside of the hollow fiber membrane to the inside thereof (from the dialysate flow route to the blood flow route) in the dialyzer 3, the blood in the blood circuit is caused to flow with the dialysate toward the tip of the arterial blood circuit 1 and the tip the venous blood circuit 2, and the blood returns into the body of the patient through the arterial puncture needle a and the venous puncture needle b.

In the course of the blood returning process S7, it is determined whether or not the blockage of the arterial blood circuit 1 (liquid flow route) is detected by the blockage detecting means 19 based on the displacement detected by the load sensor 18 (S8). The detection of the blockage of the arterial blood circuit 1 (liquid flow route) by the blockage detecting means 19 during the blood returning is as above. When the blockage of the arterial blood circuit 1 is detected in S8, the process proceeds to S5 and the notification by the notification means 20 is performed and urging the medical staff or the like to take action is performed.

In a case where it is determined that the blockage of the arterial blood circuit 1 is not detected in S8, the process proceeds to S9, and it is determined whether or not the blood returning is ended. In S9, when it is determined that the blood returning is not ended, the process returns to S7 and the detection of the blockage of the arterial blood circuit 1 is continuously performed in the blood returning process S7. On the other hand, when it is determined that the blood returning ends in S9, a discharge process S10 which drains liquid from the dialyzer 3 is performed, and a series of control operations ends. Through the series of above processes, in the dialysis treatment (blood purification treatment) and the returning of blood, it is possible to detect the blockage of the arterial blood circuit 1 in real time and it is possible to monitor the blood removing state and the blood returning state.

In the blood returning process S7, it is possible to employ any method among various methods in which the blood in the blood circuit returns into the body of the patient. For example, the blood pump 4 is caused to normally rotate and the blood from a connection section (a connection portion of T shape tube T) of the arterial blood circuit 1 with the physiological saline solution supplying line L3 to the tip of the venous blood circuit 2 is replaced with the physiological saline solution (other substitution solutions may be used) supplied from the physiological saline solution supplying line L3. In this way, the blood from the connection section to the tip of the venous blood circuit 2 returns into the patient and, after the blood circuit is filled with the physiological saline solution (substitution solution), the blood pump 4 is caused to reversely rotate and back-filtration of the dialysate is performed from the dialysate flow route to the blood flow route in the dialyzer 3, the physiological saline solution (substitution solution), with which the blood circuit is filled, is caused to flow with the dialysate, and the blood from the connection section to the tip of the arterial blood circuit 1 may return into the patient. In this case, in the blood returning process S7, the normal rotation and the reverse rotation of the blood pump 4 are performed and it is possible to detect the blockage of the arterial blood circuit 1 by the blockage detecting means 19 at the time of normal rotation and the reverse rotation.

In the blood pump 4 according to the present embodiment, since the load sensor 18 (displacement detecting means) which can detect the displacement of the peristaltically-actuated tube 1a mounted on the mounting concave section 8a in the radial direction and the blockage detecting means 19 that can detect the blockage of the arterial blood circuit 1 (liquid flow route) based on the displacement detected by the load sensor 18 are provided, it is possible to detect the blockage of the arterial blood circuit 1 without connecting a new separate member (for example, a pressure detecting unit referred to as a pillow in the related art) to the arterial blood circuit 1 (liquid flow route).

In addition, since the detection of the blockage of the arterial blood circuit 1 is performed by the blockage detecting means 19 based on the output waveform obtained through a continuous detection of the displacement performed by the load sensor 18 (displacement detecting means) while the rotor 9 is caused to rotate such that the peristaltically-actuated tube 1a is peristaltically actuated by the roller 10 (peristalsis section) in a cycle, it is possible to perform detection of the blockage of the arterial blood circuit 1 smoothly and with high accuracy.

Further, since the blockage detecting means 19 performs the detection of the blockage of the arterial blood circuit 1 based on the amplitude and cycle of the output waveform, it is possible to perform the detection of the blockage of the arterial blood circuit 1 simply and with high accuracy. Furthermore, according to the present embodiment, since the peristaltically-actuated tube 1a is connected to the intermediate portion of the arterial blood circuit 1 for performing extracorporeal circulation of blood of the patient at the time of blood purification treatment and is configured such that the detection of the blockage of the arterial blood circuit 1 during the blood purification treatment and the detection of the blockage of the arterial blood circuit 1 at the time of returning blood after the blood purification treatment can be detected, it is possible to detect negative pressure which is produced due to the blockage of the arterial blood circuit 1 at the time of removing blood and to detect positive pressure which is produced due to the blockage of the arterial blood circuit 1 at the time of returning blood.

It is possible to perform the detection of the pressure variation in the arterial blood circuit 1 at the time of removing blood and at the time of returning blood, as well as the detection of the blockage of the arterial blood circuit 1, based on the output waveform obtained through a continuous detection of the displacement performed by the load sensor 18 (displacement detecting means) while the rotor 9 is caused to rotate such that the peristaltically-actuated tube 1*a* is peristaltically actuated by the roller 10 (peristalsis section) in a cycle.

In addition, the grasping means (upstream-side grasping means 12 and downstream-side grasping means 13) for grasping the peristaltically-actuated tube 1*a* mounted on the mounting concave section 8*a* is provided and the load sensor 18 (displacement detecting means) can detect the displacement of the portion grasped by the upstream-side grasping means 12 in the radial direction. Therefore, the peristaltically-actuated tube 1*a* is mounted on the mounting concave section 8*a* so as to be grasped by the upstream-side grasping means 12, thereby, it is possible to detect the displacement and to detect the blockage of the arterial blood circuit 1 (liquid flow route) by the load sensor 18 (displacement detecting means), and thus, it is possible to lower a work burden on medical staff or the like. That is, according to the present embodiment, it is possible to perform the detection of the blockage of the arterial blood circuit 1 (liquid flow route) and it is possible to lower the work burden (time constraint) of the medical staff because there is no need to monitor the pillar or the like for detecting the negative pressure (negative pressure detecting member) during the treatment.

Further, the grasping means (upstream-side grasping means 12 according to the present embodiment) includes the grasping piece 14 that presses the peristaltically-actuated tube 1*a* in the radial direction so as to grasp the peristaltically-actuated tube 1*a* and the torsion spring 15 (biasing means) that biases the grasping piece 14 to the peristaltically-actuated tube 1*a* side. The load sensor 18 (displacement detecting means) detects a load imparted on the fixed end side of the torsion spring 15 and detects the displacement of the peristaltically-actuated tube 1*a* in the radial direction based on the detected load. Therefore, it is possible for the peristaltic pump to fulfill both a function of enabling the biasing means in the blood pump 4 (peristaltic pump) to generate a grasping force with respect to the peristaltically-actuated tube 1*a* and a function of detecting the displacement of the peristaltically-actuated tube 1*a* in the radial direction by the load sensor 18 (displacement detecting means). According to the present embodiment, it is possible to provide a blood purification apparatus in which the blood pump 4 (peristaltic pump) described above is provided.

In the blood pump 4 described above, it is possible to detect pressure of the arterial blood circuit 1 (liquid flow route) by the load sensor 18 as the displacement detecting means that detects the displacement of the peristaltically-actuated tube 1*a* in the radial direction. Therefore, there is no need to connect separate means to the arterial blood circuit 1, it is possible to suppress stagnation of the circulated liquid, and it is possible to reduce a manufacturing cost and capacity (priming volume) of the arterial blood circuit 1 (and the entire blood circuit).

Next, another embodiment of the present invention will be described.

The peristaltic pump according to the present embodiment is formed to have the blood pump which is provided on the blood circuit (specifically, the arterial blood circuit) for performing the blood purification treatment (for example, the hemodialysis treatment) by the extracorporeal circulation of the blood of the patient. Therefore, the blood circuit to which the peristaltic pump is applied is the same as in the first embodiment. Since the blood circuit (the liquid flow route and the peristaltically-actuated tube 1*a*) to which the peristaltic pump is applied is the same as that illustrated in FIG. 1 according to the precedent embodiment, description thereof is omitted.

As illustrated in FIGS. 12 and 13, a blood pump 4' (peristaltic pump) according to the present embodiment is configured mainly to have the stator 8, the rotor 9 that can rotate in the stator 8, the roller 10 (peristalsis section) formed in the rotor 9, the pair of upper and lower guide pins 11, upstream-side grasping means 12', the downstream-side grasping means 13, and a pressure transducer 21 as the displacement detecting means. The same reference numbers are attached to the same components as those in the first embodiment in the blood pump 4' and the description thereof is omitted.

The upstream-side grasping means 12' grasps the upstream side (a portion to which the tip side of the arterial blood circuit 1 is connected) of the peristaltically-actuated tube 1*a* mounted on the mounting concave section 8*a* of the stator 8 in the blood pump 4'. As illustrated in FIG. 13, the upstream-side grasping means 12' includes the grasping piece 14 that presses the peristaltically-actuated tube 1*a* in the radial direction so as to grasp the peristaltically-actuated tube 1*a* and the torsion spring 15 (biasing means) that biases the grasping piece 14 to the peristaltically-actuated tube 1*a* side.

The pressure transducer 21 as the displacement detecting means can detect the displacement in the radial direction of a portion of the peristaltically-actuated tube 1*a* which is grasped by the upstream-side grasping means 12'. According to the present embodiment, the pressure transducer 21 is provided on the portion facing the grasping piece 14 with the peristaltically-actuated tube 1*a* interposed therebetween, detects pressure which is imparted on the side surface of the peristaltically-actuated tube 1*a* pressed by the grasping piece 14, and detects displacement of the peristaltically-actuated tube 1*a* in the radial direction based on the detected pressure.

That is, when the blood is collected from the patient and is caused to flow in the arterial blood circuit 1, pressure of the liquid in the peristaltically-actuated tube 1*a* is lowered when the negative pressure is produced between the tip of the arterial blood circuit 1 and the blood pump 4' and the portion of the peristaltically-actuated tube 1*a* which is grasped by the upstream-side grasping means 12' tends to be displaced (the diameter becomes small) in the radial direction. Therefore, the contact area with the pressure transducer 21 becomes small such that the pressure detected by the pressure transducer 21 is lowered. The pressure reduction is detected and thereby, it is possible to detect the negative pressure of the arterial blood circuit 1 and to detect the blockage of the arterial blood circuit 1 by the blockage detecting means 19.

In the blood pump 4' described above, the pressure transducer 21 as the displacement detecting means which detects the displacement of the peristaltically-actuated tube 1a in the radial direction can detect the pressure of the arterial blood circuit 1 (liquid flow route). Therefore, there is no need to connect separate means to the arterial blood circuit 1, it is possible to suppress the stagnation of the circulated liquid, and it is possible to reduce a manufacturing cost and capacity (priming volume) of the arterial blood circuit 1 (and the entire blood circuit).

In addition, the blood pump 4' is provided with the grasping means (the upstream-side grasping means 12' and the downstream-side grasping means 13) for grasping the peristaltically-actuated tube 1a mounted on the blood pump 4' and the pressure transducer 21 as displacement detecting means can detect the displacement of the portion grasped by the upstream-side grasping means 12' in the radial direction. Therefore, the peristaltically-actuated tube 1a is mounted on the blood pump 4' and is grasped by the upstream-side grasping means 12' and thereby, the peristaltically-actuated tube 1a is mounted such that it is possible to reduce work burden of the medical staff or the like.

Further, the upstream-side grasping means 12' includes the grasping piece 14 that presses the peristaltically-actuated tube 1a in the radial direction so as to grasp the peristaltically-actuated tube 1a and the torsion spring 15 (biasing means) that biases the grasping piece 14 to the peristaltically-actuated tube 1a side. The pressure transducer 21 as the displacement detecting means is provided on the portion facing the grasping piece 14 with the peristaltically-actuated tube 1a interposed therebetween, detects pressure which is imparted on the side surface of the peristaltically-actuated tube 1a pressed by the grasping piece 14, and detects displacement of the peristaltically-actuated tube 1a in the radial direction based on the detected pressure. Therefore, it is possible for the peristaltic pump to fulfill both a function of enabling the displacement detecting means (pressure transducer 21) in the blood pump 4' to receive a pressing force against the peristaltically-actuated tube 1a and a function of detecting the displacement of the peristaltically-actuated tube 1a in the radial direction.

As is clear from the present embodiment, a scope of the present invention is not limited to a case where, the displacement of the peristaltically-actuated tube in the radial direction at a portion of the liquid flow route, at which the displacement detecting means is positioned actually occurs, as in the precedent embodiment, but a case where, for example, the grasping means confines and interposes both sides of the tube such that the side surfaces are confined so as not to be displaced, although a force to make displacement in the radial direction acts on the side surfaces, is also included in the scope. That is, according to the invention, it is sufficient for the displacement of the peristaltically-actuated tube 1a in the radial direction to be detected directly or indirectly and, similar to the present embodiment, the displacement produced when there is no confinement may be detected.

Here, similar to the case in FIG. 1, the blockage detecting means 19 and the notification means 20 are electrically connected to the pressure transducer 21 as the displacement detecting means described above. The blockage detecting means 19 and the notification means 20 are the same as in the embodiment described above and are configured to detect the blockage of the arterial blood circuit 1 (liquid flow route) based on the displacement detected by the pressure transducer 21 (displacement detecting means).

As above, the present embodiment is described: however, the present invention is not limited thereto. For example, instead of the blood pump, the present invention can be applied to another peristaltic pump (for example, a substitution pump or the like provided at an intermediate portion of the substitution distributing route for distributing substitution fluid at the time of blood purification treatment (blood dialysis treatment)). In addition, according to the above embodiment, the displacement detecting means is formed to include the load sensor 18 or the pressure transducer 21, detects the load or pressure, and detects the displacement of the peristaltically-actuated tube 1a in the radial direction based on the detected load or pressure; however, the present invention is not limited thereto. For example, the displacement (change of size) of the peristaltically-actuated tube 1a may be detected directly. Further, according to the above embodiment, the liquid flow route, to which the invention is applied, is the arterial blood circuit 1; however, the invention may be applied to another shape of a liquid flow route as long as the peristaltically-actuated tube is connected at a portion thereof.

INDUSTRIAL APPLICABILITY

The present invention can be applied to any peristaltic pump that includes displacement detecting means that can detect displacement of a peristaltically-actuated tube in the radial direction mounted on the mounting concave section and blockage detecting means that can detect a blockage of a liquid flow route based on the displacement detected by the displacement detecting means, even when the peristaltic pump has a different outer shape or another function is added thereto.

REFERENCE SIGNS LIST 1 arterial blood circuit (liquid flow route)
1a peristaltically-actuated tube
2 venous blood circuit
3 dialyzer (blood purifier)
4,4' blood pump (peristaltic pump)
5 arterial air trap chamber
6 venous air trap chamber
7 containing means
8 stator
9 rotor
10 roller (peristalsis section)
11 guide pin
12, 12' upstream-side grasping means
13 downstream-side grasping means
14 grasping piece
15 torsion spring (biasing means)
16 grasping piece
17 torsion spring
18 load sensor (displacement detecting means)
19 blockage detecting means
20 notification means
21 pressure transducer (displacement detecting means)

The invention claimed is:

1. A peristaltic pump comprising:
a) a mounting concave section configured to mount a peristaltically-actuated tube connected to an arterial blood circuit, the arterial blood circuit including a liquid flow route through which a predetermined liquid is circulatable;
b) a peristalsis section which compresses the peristaltically-actuated tube mounted on the mounting concave section in a radial direction and causes the peristaltically-actuated tube to be peristaltically actuated in a longitudinal direction along the peristaltically-actuated tube such that a liquid therein flows in the liquid flow route;

c) a displacement detecting means configured to detect displacement of the peristaltically-actuated tube mounted on the mounting concave section in the radial direction; and d) a blockage detecting means configured to detect a blockage of the liquid flow route based on the displacement detected by the displacement detecting means; and wherein the peristaltically-actuated tube is connected to an intermediate portion of the arterial blood circuit for extracorporeally circulating blood of a patient at time of blood purification treatment and is configured so that a blockage of the arterial blood circuit during the blood purification treatment and a blockage of the arterial blood circuit at time of returning blood after the blood purification treatment is detectable;

the peristaltic pump further comprising:

grasping means for grasping the peristaltically-actuated tube mounted on the mounting concave section, wherein the displacement detecting means is able to detect displacement of a portion grasped by the grasping means in the radial direction; and wherein the grasping means has a grasping piece that presses the peristaltically-actuated tube in the radial direction so as to grasp the peristaltically-actuated tube and biasing means that biases the grasping piece against the peristaltically-actuated tube and the displacement detecting means detects a load applied on a fixed end side of the biasing means and detects displacement of the peristaltically-actuated tube in the radial direction based on the detected load.

2. The peristaltic pump according to claim 1, further comprising:

a rotor including a plurality of peristalsis sections, wherein the rotor rotates in the mounting concave section, and thereby, the peristaltically-actuated tube mounted on the mounting concave section is peristaltically actuated by the plurality of peristalsis sections in a cycle, and the blockage detecting means performs detection of a blockage of the liquid flow route, based on an output waveform obtained by a continuous detection of the displacement performed by the displacement detecting means while the rotor is rotated such that the peristaltically-actuated tube is peristaltically actuated by the plurality of peristalsis sections.

3. The peristaltic pump according to claim 2, wherein the blockage detecting means detects a blockage of the liquid flow route based on an amplitude or a cycle of the output waveform.

4. A blood purification apparatus comprising:
the peristaltic pump to claim 1.

5. The peristaltic pump according to claim 1, wherein the displacement detecting means detects displacement of the peristaltically-actuated tube mounted on the mounting concave section in the radial direction based on a detected load or a detected pressure.

6. The peristaltic pump according to claim 5, wherein the displacement detection means is a load sensor and the blockage detecting means is configured of a microcomputer and wherein the blockage detecting means is electrically connected to the displacement detection means.

7. The peristaltic pump according to claim 6, further including a notification means electrically connected to the blockage detecting means.

8. The peristaltic pump according to claim 5, wherein the displacement detection means is a pressure transducer and the blockage detecting means is configured of a microcomputer and wherein the blockage detecting means is electrically connected to the displacement detection means.

9. The peristaltic pump according to claim 8, further including a notification means electrically connected to the blockage detecting means.

10. A peristaltic pump comprising:

a) a mounting concave section configured to mount a peristaltically-actuated tube connected to an arterial blood circuit, the arterial blood circuit including a liquid flow route through which a predetermined liquid is circulatable;

b) a peristalsis section which compresses the peristaltically-actuated tube mounted on the mounting concave section in a radial direction and causes the peristaltically-actuated tube to be peristaltically actuated in a longitudinal direction along the peristaltically-actuated tube such that a liquid therein flows in the liquid flow route;

c) a displacement detecting means configured to detect displacement of the peristaltically-actuated tube mounted on the mounting concave section in the radial direction; and d) a blockage detecting means configured to detect a blockage of the liquid flow route based on the displacement detected by the displacement detecting means; and wherein the peristaltically-actuated tube is connected to an intermediate portion of the arterial blood circuit for extracorporeally circulating blood of a patient at time of blood purification treatment and is configured so that a blockage of the arterial blood circuit during the blood purification treatment and a blockage of the arterial blood circuit at time of returning blood after the blood purification treatment is detectable;

the peristaltic pump further comprising:

grasping means for grasping the peristaltically-actuated tube mounted on the mounting concave section, wherein the displacement detecting means is able to detect displacement of a portion grasped by the grasping means in the radial direction; and wherein the grasping means has a grasping piece that presses the peristaltically-actuated tube in the radial direction so as to grasp the peristaltically-actuated tube and biasing means that biases the grasping piece against the peristaltically-actuated tube and the displacement detecting means is provided on a portion facing the grasping piece with the peristaltically-actuated tube interposed therebetween, detects pressure which is imparted on a side surface of the peristaltically-actuated tube pressed by the grasping piece, and detects displacement of the peristaltically-actuated tube in the radial direction based on the detected pressure.

11. The peristaltic pump according to claim 10, further comprising:

a rotor including a plurality of peristalsis sections, wherein the rotor rotates in the mounting concave section, and thereby, the peristaltically-actuated tube mounted on the mounting concave section is peristaltically actuated by the plurality of peristalsis sections in a cycle, and the blockage detecting means performs detection of a blockage of the liquid flow route, based on an output waveform obtained by a continuous detection of the displacement performed by the displacement detecting means while the rotor is rotated such that the peristaltically-actuated tube is peristaltically actuated by the plurality of peristalsis sections.

12. The peristaltic pump according to claim 11, wherein the blockage detecting means detects a blockage of the liquid flow route based on an amplitude or a cycle of the output waveform.

13. A blood purification apparatus comprising:
the peristaltic pump according to claim 10.

14. The peristaltic pump according to claim 10, wherein the displacement detecting means detects displacement of the peristaltically-actuated tube mounted on the mounting concave section in the radial direction based on a detected load or a detected pressure.

15. The peristaltic pump according to claim 14, wherein the displacement detection means is a load sensor and the blockage detecting means is configured of a microcomputer and wherein the blockage detecting means is electrically connected to the displacement detection means.

16. The peristaltic pump according to claim 15, further including a notification means electrically connected to the blockage detecting means.

17. The peristaltic pump according to claim 14, wherein the displacement detection means is a pressure transducer and the blockage detecting means is configured of a microcomputer and wherein the blockage detecting means is electrically connected to the displacement detection means.

18. The peristaltic pump according to claim 17, further including a notification means electrically connected to the blockage detecting means.

\* \* \* \* \*